United States Patent [19]

Stüber et al.

[11] Patent Number: 5,116,962
[45] Date of Patent: May 26, 1992

[54] MATERIAL FOR AFFINITY CHROMATOGRAPHY WHICH IS A SULFATED POLYSACCHARIDE BONDED TO AN INSOLUBLE POLYMER

[75] Inventors: Werner Stüber, Lahntal; Eric-Paul Pâques, Marburg, both of Fed. Rep. of Germany

[73] Assignee: Behringwerke Aktiengesellschaft, Marburg, Fed. Rep. of Germany

[21] Appl. No.: 554,075

[22] Filed: Jul. 16, 1990

Related U.S. Application Data

[63] Continuation of Ser. No. 338,370, Apr. 13, 1989, abandoned, which is a continuation of Ser. No. 866,248, May 23, 1986, abandoned.

[30] Foreign Application Priority Data

May 25, 1985 [DE] Fed. Rep. of Germany ....... 3519011

[51] Int. Cl.⁵ ................. C08B 37/10; C08G 4/00
[52] U.S. Cl. ................. 525/54.2; 530/413; 536/18.7; 536/51; 536/21
[58] Field of Search ............ 536/18.7, 51, 21; 424/81, 18, 83, 78; 525/54.2

[56] References Cited

U.S. PATENT DOCUMENTS

| | | | |
|---|---|---|---|
| 3,842,061 | 10/1974 | Andersson et al. | 260/112 |
| 4,041,233 | 8/1977 | Fletcher et al. | 536/56 |
| 4,496,550 | 1/1985 | Lindahl et al. | 536/21 |
| 4,600,652 | 7/1986 | Solomon et al. | 428/423.3 |

OTHER PUBLICATIONS

Danishefsky et al., Chemical Abstracts, vol. 80, 1974, No. 143604r.

Ebert et al., Chemical Abstracts, vol. 97, 1982, No. 11591r.

Casu et al., Chemical Abstracts, vol. 1986, No. 199900r.

Funahashi et al., Analytical Biochemistry, vol. 126, (1982) pp. 414–421.

Kohn et al., Mechanism of Activation of Sepharose and Sephadex by Cyanogen Bromide, vol. 4, 1982, pp. 161–163.

Andersson et al., Purification of Antithrombin III by Affinity Chromatography, vol. 5, No. 4, 1974, pp. 439–452.

Porath et al., Journal of Chromatography, 51, 1970, pp. 479–489.

Sundberg et al., Journal of Chromatography, 90, 1974, pp. 87–98.

Isamu et al., Journal of Chromatography, 239, 1982, pp. 747–754.

Primary Examiner—Johnnie R. Brown
Assistant Examiner—Elli Peselev
Attorney, Agent, or Firm—Finnegan, Henderson, Farabow, Garrett and Dunner

[57] ABSTRACT

A process for the preparation of a material for affinity chromatography is described, in which a sulfated polysaccharide is bonded to a carrier material which has amino groups.

For this purpose, a sulfated polysaccharide is treated with an oxidizing agent which oxidizes glycols to aldehydes, with cleavage of the carbon chain, and this modified sulfated polysaccharide is allowed to react with a carrier which has amino groups.

It is possible using the described affinity material to adsorb proteins which bind to sulfated polysaccharides from solutions of these proteins and, where appropriate, then to desorb them, for example antithrombin III from blood plasma.

1 Claim, No Drawings

MATERIAL FOR AFFINITY CHROMATOGRAPHY WHICH IS A SULFATED POLYSACCHARIDE BONDED TO AN INSOLUBLE POLYMER

This application is a continuation of application Ser. No. 07/338,370, filed Apr. 13, 1989, now abandoned, which was a continuation of application Ser. No. 06/866,248, filed May 23, 1986, now abandoned.

The invention relates to a process for the preparation of a material for affinity chromatography, in which a sulfated polysaccharide is bonded to a carrier material which has amino groups.

This material can be used for the isolation and purification of substances which interact with sulfated polysaccharides.

BACKGROUND OF THE INVENTION

The isolation of enzymes has been considerably improved in recent years by the technique of affinity chromatography. This method makes use of specific interactions between substances. For this purpose, a substance is covalently bonded as ligand onto an insoluble carrier (matrix). The ligand must be able to undergo an interaction, of the nature of a complex, with the substance which is to be isolated. The ligand retains only those substances which specifically react with it. Other substances are washed out. The retained substances can be eluted from the carrier material using a solution of unbonded ligand or, for example, using a salt gradient.

The success of an affinity chromatography depends on how well the interactions which naturally takes place between the substance which is to be isolated and the ligand are simulated. Thus, the choice of the matrix and the manner of immobilization of the ligand are important. The matrix ought to be hydrophilic and have good mechanical and chemical stability. Steric effects impeding the interaction can be favorably affected by spacers. Neither the matrix nor the spacer ought to give rise to non-specific adsorption.

For the isolation of a protein, it is of course most favorable to use a ligand which interacts only with one protein or with few proteins. The capacity of the adsorbent depends on the ligand loading of the matrix being sufficiently high. The chemical bonding ought to be as uniform and stable as possible, that is to say as difficult to hydrolyze as possible.

Affinity chromatography can be used for the isolation of proteins, for example from plasma, especially of antithrombin III. Immobilized sulfated polysaccharides have proved useful as affinity material for this purpose, especially carrier-bound heparin. However, it is known that, on immobilization of heparin and other sulfated polysaccharides, modifications of the ligand, with a reduction in biological activity, may occur.

The present invention had the object of preparing a material for affinity chromatography, by covalently bonding a sulfated polysaccharide to a carrier so that a material with high biological activity, ligand density and stability is obtained.

PRIOR ART

Affinity chromatography, especially using heparin, is utilized for the isolation of proteins which form complexes with sulfated polysaccharides.

For this purpose, a sulfated polysaccharide is bonded to a suitable carrier, the polysaccharide frequently being the mucopolysaccharide heparin. SEPHAROSE ® 4B (an agarose gel in bead form; Pharmacia, Sweden) has proved especially useful as carrier matrix.

The covalent bonding of a sulfated polysaccharide to the carrier is mainly accomplished by activation of the carrier material or of the sulfated polysaccharide with cyanogen bromide (Thromb.Res. 5, 439–452 (1974), German Offenlegungsschrift 2,243,688). However, this method has associated deficiencies. The isourea links which are formed between amino groups of ligands and hydroxyl groups of customary carrier materials are to a certain extent unstable toward nucleophilic reagents. This means that detachment of ligands must be expected under the conditions of elution, especially at elevated pH (Enzyme Microb. Technol. 4, 161–163, 1981).

This disadvantage can be eliminated by replacement of the cyanogen bromide by activators which contain oxirane groups. It is possible using epichlorohydrin (J.Chromatogr. 51, 479, 1970) or using bis-oxiranes, such as 1,4-butanediol bis(epoxypropyl) ether (J.Chromatogr. 90, 87, 1974), to introduce oxirane groups into a matrix which contains hydroxyl groups. The oxirane groups which have been introduced can be converted into amino groups with ammonia. It is possible using a carbodiimide (Anal. Biochem. 126, 414–421, 1982) to bond a sulfated polysaccharide which contains carboxyl groups to these amino groups.

The resulting amide bonds are distinguished by high chemical stability. The disadvantage of this method is that a number of carboxyl groups is converted into N-acylurea derivatives during the activation with carbodiimides. This means that although this process accomplishes extensive loading of the carrier with sulfated polysaccharides, nevertheless, as a consequence of their chemical modification, relatively low binding capacities are available for the substances which are to be isolated by affinity chromatography.

However, the bonding of a sulfated polysaccharide to a carrier material into which amino groups have been introduced can be accomplished in a chemically unambiguous manner by reductive coupling (Analyt.Biochem. 126, 414–421, 1982). This entails the reducing end (aldehyde group) of the saccharide chain being coupled to an amino group of a polymer, with the formation of a Schiff's base. To stabilize the C=N double bonds they are reduced, for example with sodium cyanoborohydride, to the secondary amine. This method allows adequate loading of SEPHAROSE ® 4B, into which amino groups have been introduced, with, for example, heparin, but it cannot be straightforwardly applied to other polymers.

In place of SEPHAROSE ® 4B, which is widely used, it is in principle possible to use other polymers which contain hydroxyl groups as the carrier material, for example FRACTOGEL ® HW-65 (F) (a synthetic hydrophilic polymer containing hydroxyl groups; J.Chromatogr. 239, 747–754, 1982). This polymer is, by reason of its chemical and physical properties, frequently more favorable than SEPHAROSE ® 4B for industrial use.

However, there is no known process for bonding FRACTOGEL ® HW-65 (F), after introduction of amino groups, to the reducing end of a sulfated polysaccharide in satisfactory yield.

The process described in this application does not have the disadvantages of the prior art and it makes it possible to couple, with good yields, a suitably derivatized sulfated polysaccharide to a carrier material into which amino groups have been introduced.

SUMMARY OF THE INVENTION

In the process described, sulfated polysaccharides are modified with a diol-cleaving oxidizing agent, additional aldehyde groups thus being produced on the polysaccharide. Derivatives of this type can be bonded in good yields to carriers into which amino groups have been introduced. The resulting Schiff's bases can be reduced to the amine with reducing agents, for example sodium cyanoborohydride.

Thus the invention relates to a process for the preparation of a sulfated polysaccharide bonded to a carrier, which comprises treatment of a sulfated polysaccharide with an oxidizing agent which oxidizes glycols to aldehydes, with cleavage of the carbon chain, and reaction of this modified sulfated polysaccharide with a carrier which has amino groups.

It is possible to use as starting material one of the known sulfated polysaccharides, preferably heparin or its sodium salt. Aldehyde groups have been generated in aqueous solution by treatment with an oxidizing agent known to react with diols to form aldehyde groups, preferably an alkali metal periodate. The pH of the reaction solution was maintained in the range 5-9, preferably 6-8, with a base, preferably an alkali metal hydroxide, especially lithium hydroxide. 5-100 mg of alkali metal periodate, preferably 30-40 mg of sodium periodate, per gram of heparin have proved particularly favorable. The reaction times are in the range from 10 min to 5 hours, the reaction temperature being maintained at between 0° and 30° C. The oxidation reaction is preferably carried out for one hour at 4° C.

For coupling the polyaldehyde-derivatized sulfated polysaccharide it is possible to add the oxidation mixture directly to a carrier into which amino groups have been introduced. Carriers into which amino groups have been introduced are described in Analyt.Biochem. 126, 414–421 (1982).

The following are suitable as carrier materials for functionalization:

Insoluble polymers which contain hydroxyl groups and into which amino groups can be introduced in a suitable manner, such as polymers based on carbohydrates. These include dextran and agarose resins as well as copolymers of methacrylic acid derivatives, pentaerythritol, polyethylene glycol and divinylbenzene, which are marketed under the name FRACTOGEL ®.

A carrier into which amino groups have been introduced in this manner is reacted with a polyaldehyde-derivatized polysaccharide, preferably 30-40 g of polysaccharide with 1,000 ml of carrier. The reaction is carried out at pH 6-9, preferably at room temperature and preferably in a buffered aqueous solution, in particular at pH 6-7 in a phosphate buffer. After the reactants have been mixed, an alkali metal borohydride, such as sodium cyanoborohydride is added. The reaction at room temperature takes 1 to 30 days. The preferred reaction time is 12 to 16 days. The product is washed with water and treated with acetic anhydride, by which means amino groups which are still free are acetylated.

It is known that, using suitable oxidizing agents, diols having hydroxyl groups on adjacent carbon atoms (glycols), such as, for example, sugars, provide aldehyde groups with cleavage of the carbon-carbon bond. Surprisingly, the action of the necessary "strong" oxidizing agents did not result in a loss of biological activity of the sulfated polysaccharide, and heparin which has been polyaldehyde-derivatized by the described process exhibited high binding affinity for and activity toward proteins which form complexes with heparin. This biological activity is also retained in the derivatives bonded to the carrier. A favorable coupling behavior is achieved owing to the large number of aldehyde groups in the ligands, since the coupling yields depend not only on the number of amino groups on the carrier but also on the number of aldehyde groups on the ligand. Carriers with few amino groups require a large number of reactive aldehyde groups.

The binding capacity of the adsorbent for the protein which is to be adsorbed depends directly on the ligand loading.

It is possible using the affinity materials obtained in the described manner to adsorb proteins which bind to sulfated polysaccharides from solutions of these proteins and, where appropriate, then to desorb them, for example antithrombin III from blood plasma. The effect of the number of amino groups in the resins on the coupling yields for heparin and polyaldehyde-derivatized heparin has been demonstrated with the polymers which are preferably used, SEPHAROSE ® 4B and FRACTOGEL ® HW-65 (F).

When a heparin which had been polyaldehyde-derivatized by this method was bonded to amino-SEPHAROSE 4B it emerged that the binding capacity for antithrombin III was up to 2.5-fold that of a material which had been prepared from heparin and amino-SEPHAROSE by a known method. The differences were even more drastic with carriers having lower numbers of amino groups, for example amino-FRACTOGEL HW-65(F). Owing to the additional aldehyde groups, the binding capacity increased to 2 to 5 times that for the unmodified immobilized ligand.

By reason of the chemical nature of the ligand linkage, there was a very low tendency to lose ligands shown by the adsorbents which had been prepared using the derivatized (oxidized) sulfated polysaccharides. Compared with a ligand immobilized via isourea links, as are produced by activation with cyanogen bromide, the loss of ligands under comparable conditions was reduced by the described process to 0.1 to 1%.

EXAMPLE 1

Introduction of amino groups into SEPHAROSE ® 4B 1,500 ml of water and 650 ml of 2N sodium hydroxide solution were added to 1,000 ml of thoroughly washed SEPHAROSE ® 4B. This suspension was heated to 40° C., 150 ml of epichlorohydrin were added, and the mixture was shaken at 40° C. for two hours. The product was washed to neutrality with water, and was treated with 750 ml of ammonia solution (density 0.91 g/ml) at 40° C. for 90 min. Washing with water to a neutral reaction was carried out to remove excess reagents.

Oxidation of the sodium salt of heparin 30 g of the sodium salt of heparin (about 160 IU/g) were dissolved in 500 ml of water, and the pH was adjusted to 7 with a 20 g/l lithium hydroxide solution. This solution was cooled to 4° C., and 1.2 g of sodium periodate were added. The oxidation was continued for one hour, the pH being maintained at 7 by dropwise addition of a 20 g/l lithium hydroxide solution. This solution was used immediately for the coupling to the carrier into which amino groups had been introduced.

Coupling of oxidized heparin to amino-SEPHAROSE 4B 1,000 ml of SEPHAROSE ® 4B into which amino groups had been introduced were suspended in 1,000 ml of 0.2 mol/l dipotassium hydrogen phosphate buffer, pH 9. 30 g of oxidized heparin and 11.5 g of sodium cyanoborohydride were added to this suspension. The mixture was stirred at room temperature for 16 days, and the solid was filtered off and thoroughly washed with water. The product was suspended in 1,000 ml of 0.2 mol/l of sodium acetate solution and, at 4° C., 500 ml of acetic anhydride were added. Washing with water to neutrality was carried out after 30 min.

EXAMPLE 2

Introduction of amino groups into FRACTOGEL ® HW-65 (F)

325 ml of water and 275 ml of 5 normal sodium hydroxide solution were added to 1,000 ml of FRACTOGEL ® HW-65 (F). 200 ml of epichlorohydrin were added to this mixture, which was shaken at 45° C. for two hours. The product was filtered off and washed several times with water. The introduction of the amino groups was carried out with 500 ml of ammonia solution (density 0.91 g/ml) at 45° C. for 90 min. The resin was then filtered off and washed with water to neutrality.

Coupling of oxidized heparin to FRACTOGEL ® HW-65 (F) into which amino groups have been introduced 1,000 ml of amino-FRACTOGEL ® HW-65 (F) were suspended in 500 ml of 0.5 mol/l sodium phosphate buffer, pH 6.5, and 30 g of heparin oxidized as in Example 1 were added. The pH was maintained at 6.5 with ortho-phosphoric acid (850 g/l solution). 11.5 g of sodium cyanoborohydride dissolved in 30 ml of water were added to this suspension. It was stirred at room temperature for 16 days, and the solid was filtered off and washed with water. The product was suspended in 100 ml of 0.2 mol/l sodium acetate solution, and 500 ml of acetic anhydride were added, and the mixture was stirred at 4° C. for 30 min. The solid was filtered off with suction and washed with water.

I claim:

1. A sulfated polysaccharide bonded to an insoluble polymer prepared by a process which comprises treating a sulfated polysaccharide selected from the group consisting of heparin and its sodium salt with an alkali metal periodate which oxidizes glycols to aldehydes, thereby cleaving the carbon chain, and reacting the modified sulfated polysaccharide with an insoluble polymer containing amino groups selected from the group consisting of dextran resins, agarose resins and copolymers of methacrylic acid derivatives, pentaerythritol, polyethylene glycol and divinylbenzene.

* * * * *